United States Patent [19]

Jackson

[11] 4,022,607
[45] May 10, 1977

[54] SUBSTITUTED OXAZOLES AND THIAZOLES AS HERBICIDES

[75] Inventor: Thomas E. Jackson, Madison, N.J.

[73] Assignee: Sandoz, Inc., E. Hanover, N.J.

[22] Filed: June 9, 1975

[21] Appl. No.: 584,885

[52] U.S. Cl. .................................. 71/88; 71/90; 260/302 S; 260/307 R
[51] Int. Cl.² ...................... A01N 9/12; A01N 9/14
[58] Field of Search ................................ 71/90, 88

[56] References Cited

UNITED STATES PATENTS

| | | | |
|---|---|---|---|
| 2,693,408 | 11/1954 | D'Amico | 71/90 X |
| 2,769,010 | 10/1956 | D'Amico | 71/88 X |
| 2,776,976 | 1/1957 | D'Amico | 71/90 X |
| 3,475,445 | 10/1969 | Hyatt | 71/90 X |

Primary Examiner—Joseph Paul Brust
Attorney, Agent, or Firm—Gerald D. Sharkin; Richard E. Vila; Joseph J. Borovian

[57] ABSTRACT

Substituted oxazoles and thiazoles are useful as herbicides.

22 Claims, No Drawings

SUBSTITUTED OXAZOLES AND THIAZOLES AS HERBICIDES

The present invention relates to substituted oxazoles and thiazoles, their use as herbicides and compositions containing the same for use as herbicides.

The compounds which are the subject of the present invention may be represented by the following structural formula I:

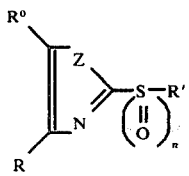
I wherein R° and R are independently hydrogen, alkyl of 1 to 6 carbon atoms, phenyl or substituted phenyl of the formula:

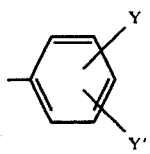

in which
Y is fluoro, chloro, bromo, alkyl of 1 to 4 carbon atoms, alkoxy of 1 to 4 carbon atoms, trifluoromethyl, phenyl or phenoxy, and
Y' is hydrogen, fluoro, chloro, bromo, alkyl of 1 to 4 carbon atoms or alkoxy of 1 to 4 carbon atoms
R' is alkyl of 1 to 6 carbon atoms,
Z is oxygen or sulfur, and
n is 0, 1 or 2.

The compounds of the formula I having the formula IA:

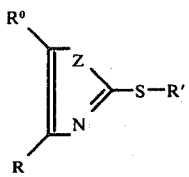
IA wherein Z, R°, R and R' are as defined, may be prepared by alkylating a compound of the formula II:

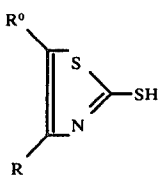
II wherein R° and R are as defined, by conventional techniques. Such preparation is suitably carried out by reacting a compound II with a compound III:

 — R'    III wherein R' is as defined and X is chloro, bromo, iodo, or a leaving group such as sulfate and the like, in the presence of a base and in an inert solvent at a temperature of from 0° to 150° C., preferably 10° to 60° C. Suitable bases are of the organic and inorganic type such as an alkali metal hydroxide, triethylamine and pyridine. Preferred solvents are water and/or water-miscible solvents such as the lower alkanols, e.g., ethanol, more preferably water and ethanol.

The compounds I of the formula IB:

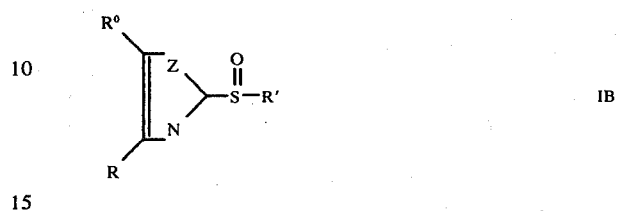
IB wherein R°, R, R' and Z are as defined, may be prepared by oxidizing a compound IA.

The preparation of compounds of formula IB involves the reaction of a compound of the formula IA above with not more than an equimolar amount of oxidizing agent such as a peracid, e.g., m-chloro-peroxybenzoic acid, in the presence of an inert, organic solvent which is adapted to dissolving the reactants and product compounds of formula IB. Suitable solvents are known and available, and include by way of illustration, the chlorinated hydrocarbons, nitrated hydrocarbons, e.g., nitromethane, lower alkanols, e.g., ethanol, and ethers, e.g., dioxane, tetrahydrofuran, etc. The reaction is preferably effected in the presence of a chlorinated hydrocarbon, e.g., methylene chloride. The reaction may be carried out at temperatures in the range of from −20° to 70° C., preferably −5° to 25° C., and most preferably, between 0° and 10° C. The reaction product of formula IB may be isolated from the reaction mixture by working up by conventional techniques.

The compounds of the formula I having the formula IC:

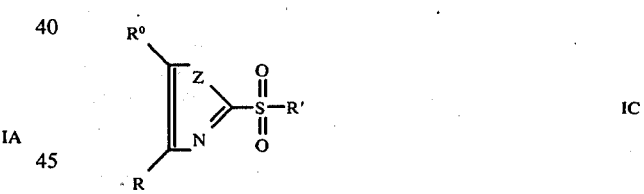
IC wherein R°, R, R' and Z are as above defined, may be prepared by oxidizing a compound of the formula IA or IB in the same manner as the compound IB is prepared from compound IA as above described, except that an appropriate molar amount or excess of the oxidizing agent is employed, preferably a peracid.

The compounds of the formulae II and III are either known per se or may be prepared in conventional manner from available materials, e.g., by Kjellin & Sandstrom, Acta Chem. Scand., 23, 2879–2887 (1969), Cohen, Celeste, And Fan, Photo Sci. Eng., 9, 96–103(1965) and Gruenert And Wiechert, 2. Chem., 10, 396–7 (1970).

In accordance with the present invention, the above-indicated compounds of the formula I are useful as herbicides as indicated, for example, by a herbicidal action against a variety of weed species such as:
*Amaranthus retroflexus,*
*Capsella bursa pastoris,*
*Chenopodium album,*
*Calium aparine,*

*Stellaria media,*
*Senecio vulgaris,*
*Echinochloa crus-galli,*
*Alopecurus myosuroides* and
*Agrostis alba,*
when, for example, applied post emergens at test concentrates of 2.5 to 10 kilograms per hectare followed by examination and an observation of herbicidal effect 14 days after application.

The compounds of the present ivention, in addition to being useful in combatting weeds generally, may be used for selectively combatting weeds in a cultivated crop in which wheat, cotton or soya is being cultivated.

For the above-mentioned uses, the amount of compound to be applied to a weed infested locus will vary depending on the particular compound employed, mode of application, ambient conditions, the weeds species to be combatted and the cultivated crop, if any, involved. However, in general, a suitable amount to be applied for a locus is between 1 and 10 kg/hectare of the compound, the application to be repeated as required. For selective application to cultivated crop loci, the application of from 1 to 6 kg/hectare of a compound I is generally suitable.

The application of the compound may either be pre- or post-emergence of the weeds, and where the locus is a cultivated crop locus and the method is for the selective combatting of weeds in the cultivated crop, the compound may be applied either pre- or post-emergence of either the weeds or the crop. Preferably, the compound is applied post-emergence of the crop. The compound may be applied in the form of a herbicidal composition as herein described.

The compounds of the formula I may be employed as herbicidal compositions in association with a herbicide carrier such as a solvent and/or diluents. Such compositions also form part of the present invention.

Herbicidal compositions may be employed in either solid or liquid application forms, and prepared in conventional manner. Solid forms, e.g. dusting forms and granulates, may be produced by mixing or impregnating solid herbicide carriers such as diatomaceous earth, kaolin, talc, chalk, limestone and cellulose powder, with the compounds.

Additives may be employed in the herbicidal composition. Typical of such additives are wetting and dispersing agents, e.g. the condensation product of formaldehyde with naphthalene sulphonate, and alkyl benzene sulphonates, adhesion imparting agents, e.g. dextrin, and emulsion stabilizers, e.g. ammonium caseinate. Such additives are suitable for incorporation into, e.g. a wettable powder form of composition.

Concentrate forms of composition generally contain between 2 and 80%, preferably between 2 and 50%, by weight of a compound of formula I as active agent.

Application forms of composition generally contain between 0.01 and 10%, by weight of a compound of formula I as active agent.

APPLICATION EXAMPLE 1

A compound of the formula I, e.g., 2-methylsulfinyl-4-phenyl-5-methyl-thiazole, is applied to a wheat culture containing no weeds identified hereinabove, post-emergence with respect to both wheat and weeds, at a concentrate of 3 kg/hectare. After 14 days, no significant effect on the wheat is observed whereas a significant herbicidal effect is observed against the weeds.

APPLICATION EXAMPLE 2

A compound of the formula I, e.g., 2-methylsulfinyl-4-phenyl-5-methyl-thiazole, is applied to a cotton culture (Gossypium hirisutum) containing the following weed species:
*Sida spinosa,*
*Echinochloa crus galli,*
*Amaranthus retroflexus,*
*Ipomoea rubra,*
*Digitaria sanguinalis,*
*Chenopodium album,*
*Sisymbrium irio* and
*Postulaca oleracea.*
The application is made at a concentration of 3 kg/hectare pre-emergence and 2½ kg/hectare post-emergence. In both cases, a significant herbicidal effect against the weed species is observed with no significant effect on the cotton crop.

APPLICATION EXAMPLE 3

The application described in Example 2, above, is repeated except that the cultivated crop is soya in place of the cotton, and results in a significant herbicidal action while the soya is essentially undamaged.

Specific Examples of herbicidal compositions useful, for example, in the above-referred to tests and applications are as follows:

Example A

Wettable Powder Form of Composition 25 parts of 2-methylsulfinyl-4-phenyl-5-methyl-thiazole, 5 parts of a condensation product from formaldehyde and napthalene sulphonate, 2 parts of alkyl benzene sulphonate, 5 parts of dextrin, 1 part of ammonium caseinate and 62 parts of diatomaceous earth are mixed until a homogeneous mixture is obtained and then ground until the particles are considerably smaller than 45 microns as an average.

Example B

Wettable Powder Form of Composition 25 parts of 2-methylsulfinyl-4-phenyl-5-methyl-thiazole, 5 parts of a condensation product from formaldehyde and napthalene sulphonate, 2 parts of alkyl benzene sulphonate, 5 parts of dextrin, 1 part of ammonium caseinate and 62 parts of diatomaceous earth are mixed until a homogeneous mixture is obtained and then ground until the particles are considerably smaller than 45 microns as an average.

Specific Examples illustrating the compounds of formula I and their production will now be described. Where temperature is referred to, this is in degrees Centigrade.

EXAMPLE 1

5-methyl-2-methylthio-4-phenyl-thiazole

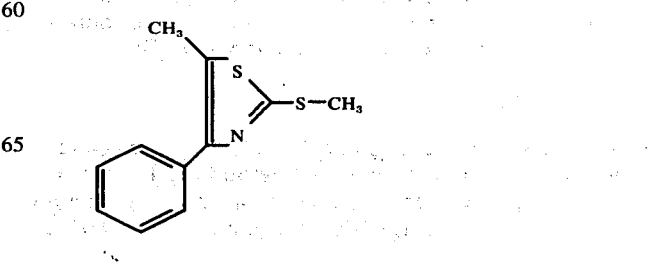

To 14.9 g. of 2-mercapto-5-methyl-4-phenyl-thiazole is added 60 ml. of water and 19.5 ml. of a 15% aqueous solution of sodium hydroxide and the mixture is stirred until most of the material dissolves. The stirred mixture is then treated with methyl iodide (5 ml.) in ethanol (20 ml.). After two hours, the reaction is complete (tlc) and the reaction mixture is extracted with ether. The combined ether extracts are washed successively with a 10% solution of sodium carbonate and brine, dried and concentrated in vacuo to an oil, b.p. 138°–140° C. at 0.04 mm Hg.

EXAMPLE 2

5-methyl-2-methylsulfinyl-4-phenyl-thiazole

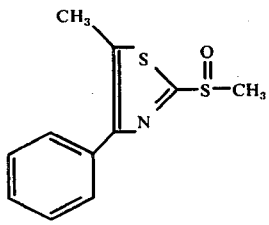

6.56 g. of 5-methyl-2-methylthio-4-phenylthiazole pre-dissolved in 100 ml. of methylene chloride is cooled in an ice bath. The stirred solution is treated with 6.01 g. of m-chloroperoxybenzoic acid, added in portions over five minutes. After 30 minutes, the reaction is complete and the precipitated m-chlorobenzoic acid is filtered and the filtrate washed successively with a 10% solution of sodium sulfite, saturated aqueous sodium bicarbonate solution and water. After drying, concentration in vacuo and chromatography yields a white solid, m.p. 96°–97° C.

EXAMPLE 3

5-methyl-2-methylsulfonyl-4-phenyl-thiazole

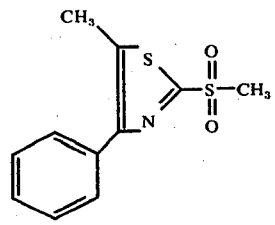

5.33 g. of 5-methyl-2-methylthio-4-phenyl-thiazole pre-dissolved in 200 ml. of methylene chloride is cooled in an ice bath. The stirred solution is treated with 12.2 g. of m-chloroperoxybenzoic acid, added in portions over five minutes. The ice bath is removed after one hour of stirring and the reaction mixture is allowed to stir for an additional three hours at room temperature to complete the reaction. The precipitated m-chlorobenzoic acid is filtered and the filtrate washed successively with a 10% solution of sodium bisulfite, saturated sodium bicarbonate solution and water. After drying, concentration in vacuo followed by recrystallization from toluene-hexane yields white needles, m.p. 114°–115° C.

EXAMPLE 4

Following the procedure of Example 1, the following compounds are prepared.
 a. 2-methylthio-4-phenyl-thiazole.
 b. 2-methylthio-4,5-diphenyl-thiazole.

EXAMPLE 5

2-methylsulfinyl-4-phenyl-thiazole

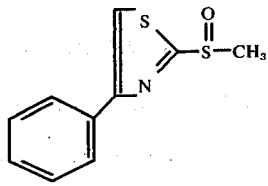

To a cooled (ice/water) solution of 8.9 g. of 2-methylthio-4-phenyl-thiazole pre-dissolved in 90 ml. of methylene chloride is added in portions over 5 minutes, 8.7 g. of m-chloro-peroxybenzoic acid. Examination by TLC after 90 minutes indicates the presence of essentially all of the sulfinyl compound (reaction complete) with a faint trace of sulfone and an even fainter trace of remaining thiazole starting material. The precipitated m-chloro-benzoic acid is filtered off and the methylene chloride solution is washed successively with a 10% solution of sodium sulfite and with saturated sodium bicarbonate solution, dried, evaporated in vacuo to dryness and the residue further dried overnight in vacuo, to yield 2-methylsulfinyl-4-phenyl-thiazole, m.p. 104°–105° C.

EXAMPLE 6

2-methylsulfinyl-4,5-diphenyl-thiazole

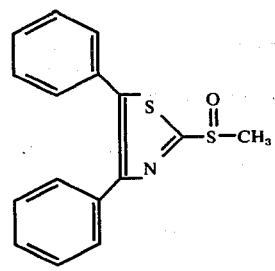

To a cooled (ice/water) solution of 1.1 g. of 2-methylthio-4,5-diphenyl-thiazole pre-dissolved in 15 ml. of methylene chloride is added in portions over 5 minutes, 0.8 g. of m-chloro-peroxybenzoic acid. Examination by TLC after 30 minutes indicates the presence of essentially all of the sulfinyl compound (reaction complete). The precipitated m-chloro-benzoic acid is filtered off and the methylene chloride solution is washed successively with a 10% solution of sodium bisulfite and with saturated sodium bicarbonate solution, dried, evaporated in vacuo to dryness and the residue further dried overnight in vacuo to yield 2-methylsulfinyl-4,5-diphenyl-thiazole, m.p. 102°–103° C.

EXAMPLE 7

Following the procedure of Example 1, the following are prepared:
 a. 2-methylthio-4-(p-chlorophenyl)-thiazole, m.p. 93°–95.5° C.
 b. 2-methylthio-4-(p-methoxyphenyl)-thiazole, m.p. 85°–86° C.
 c. 2-methylthio-4-(m-trifluoromethylphenyl)-thiazole, m.p. 71.5°–73° C.

d. 2-methylthio-5-phenyl-thiazole.
e. 2-methylthio-4-methyl-5-phenyl-thiazole.
f. 2-ethylthio-5-methyl-4-phenyl-thiazole.
g. 2-methylthio-4-p-biphenylyl-thiazole.
h. 2-methylthio-4-p-phenoxyphenyl-thiazole.

EXAMPLE 8

Following the procedure of Example 2, the following are prepared:
 a. 2-methylsulfinyl-4-(p-chlorophenyl)-thiazole, m.p. 139°-140° C.
 b. 2-methylsulfinyl-4-(p-methoxyphenyl)-thiazole, m.p. 126°-127° C.
 c. 2-methylsulfinyl-4-(m-trifluoromethylphenyl)-thiazole, m.p. 100°-101° C.
 d. 2-methylsulfinyl-5-phenyl-thiazole, m.p. 58°-59.5° C.
 e. 2-methylsulfinyl-4-methyl-5-phenyl-thiazole, as an oil.
 f. 2-ethylsulfinyl-5-methyl-4-phenyl-thiazole.
 g. 2-methylsulfinyl-4-p-biphenylyl-thiazole, m.p. 186°-188.5° C.
 h. 2-methylsulfinyl-4-p-phenoxyphenyl-thiazole.

EXAMPLE 9

Following the procedure of Example 3, the following are prepared:
 a. 2-methylsulfonyl-4-(p-chlorophenyl)-thiazole, m.p. 146°-147° C.
 b. 2-methylsulfonyl-4-(p-methoxyphenyl)-thiazole, m.p. 129°-130° C.
 c. 2-methylsulfonyl-4-(m-trifluoromethylphenyl)-thiazole, m.p. 129.5°-130.5° C.
 d. 2-methylsulfonyl-5phenyl-thiazole, m.p. 101°-102° C.
 e. 2-methylsulfonyl-4-methyl-5-phenyl-thiazole.
 f. 2-ethylsulfonyl-5-methyl-4-phenyl-thiazole.
 g. 2-methylsulfonyl-4-p-biphenylyl-thiazole, m.p. 191.5°-192.5° C.
 h. 2-methylsulfonyl-4-p-phenoxyphenyl-thiazole.
 i. 2-methylsulfonyl-4,5-diphenyl-thiazole, m.p. 135°-136° C.
 j. 2-methylsulfonyl-4-phenyl-thiazole, m.p. 142°-144° C.

EXAMPLE 10

Following the procedure of Example 1, the following are prepared:
 a. 2-methylthio-4,5-diphenyl-oxazole.
 b. 2-ethylthio-4,5-diphenyl-oxazole.
 c. 2-butylthio-4,5-diphenyl-oxazole.
 d. 2-methylthio-4-phenyl-oxazole.
 e. 2-methylthio-5-phenyl-oxazole.
 f. 2-methylthio-5-methyl-4-phenyl-oxazole.

EXAMPLE 11

2-methylsulfinyl-4,5-diphenyl-oxazole

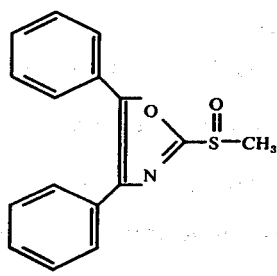

To a cooled (ice/water) solution of 5.21 g. of 2-methylthio-4,5-diphenyl-oxazole pre-dissolved in 50 ml. of chloroform is added in portions over 5 minutes, 4.35 g. of m-chloro-peroxybenzoic acid dissolved in 50 ml. of chloroform. After stirring the reaction mixture for 20 minutes, the ice/water bath is removed and the reaction mixture stirred at room temperature for an additional 60 minutes. The precipitated m-chloro-benzoic acid is filtered off, washed with chloroform and the combined chloroform solution is washed with a 10% solution of sodium carbonate, dried, evaporated in vacuo to dryness, and the residue recrystallized from benzene/ligroin to yield 2-methylsulfinyl-4,5-diphenyl-oxazole, m.p 78°-78° C.

EXAMPLE 12

2-ethylsulfinyl-4,5-diphenyl-oxazole

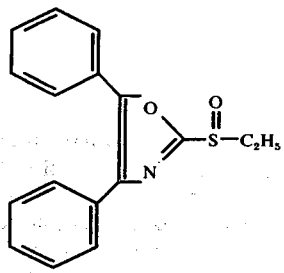

To a cooled (ice/water) solution of 4.2 g. of 2-ethylthio-4,5-diphenyl-oxazole pre-dissolved in 30 ml. of methylene chloride is added in portions over 5 minutes, 30 g. of m-chloro-peroxybenzoic acid. Examination by TLC after 2 hours indicates the presence of essentially all of the sulfinyl compound (reaction complete). The precipitated m-chloro-benzoic acid is filtered off and the methylene chloride solution is washed successively with a 10% solution of sodium sulfite and with saturated sodium bicarbonate solution, dried, evaporated in vacuo to dryness, and the residue further dried overnight in vacuo to yield 2-ethylsulfinyl-4,5-diphenyl-oxazole, m.p 133°-134° C.

EXAMPLE 13

Following the procedure of Example 2, the following are prepared:
 a. 2-butylsulfinyl-4,5-diphenyl-oxazole, m.p. 91°-92° C.
 b. 2-methylsulfinyl-4-phenyl-oxazole, m.p. 47°-50° C.
 c. 2-methylsulfinyl-5-phenyl-oxazole, b.p. 125°-130° C. (0.005 mm/Hg.).
 d. 2-methylsulfinyl-5-methyl-4-phenyl-oxazole.

EXAMPLE 14

Following the procedure of Example 3, the following are prepared:
 a. 2-methylsulfonyl-4,5-diphenyl-oxazole, m.p. 146°-147.5° C.
 b. 2-ethylsulfonyl-4,5-diphenyl-oxazole.
 c. 2-butylsulfonyl-4,5-diphenyl-oxazole.
 d. 2-methylsulfonyl-4-phenyl-oxazole.
 e. 2-methylsulfonyl-5-phenyl-oxazole.
 f. 2-methylsulfonyl-5-methyl-4-phenyl-oxazole.

Preferred herbicides of the invention are those characterized by one of the following features or two or more thereof in any combination: (a) Z is sulfur; (b) R° is hydrogen or alkyl of 1 to 6 carbon atoms; (c) R is phenyl or substituted phenyl as above defined; and (d) n is 1.

The more preferred herbicides of the formula I are those in which Z is sulfur, n is 1, R° is alkyl of 1 to 6 carbon atoms and R is phenyl or phenyl mono-or disubstituted by fluoro, chloro, bromo, alkyl of 1 to 4 carbon atoms, alkoxy of 1 to 4 carbon atoms or trifluoromethyl.

In the preferred and more preferred compounds R' and R° (when alkyl) are preferably of 1 to 3 carbon atoms, more preferably methyl, and any alkyl or alkoxy substituent of R when substituted phenyl is preferably methyl or ethyl, more preferably methyl.

Novel compounds provided by the invention include those of the formula:

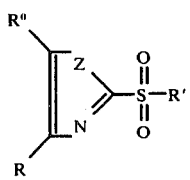

wherein
R' is alkyl of 1 to 6 carbon atoms,
Z is oxygen or sulfur,
R° is hydrogen or alkyl of 1 to 6 carbon atoms, and
R is phenyl or substituted phenyl of the formula:

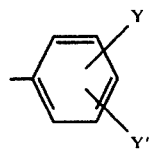

in which
Y is fluoro, chloro, bromo, alkyl of 1 to 4 carbon atoms, alkoxy of 1 to 4 carbon atoms, trifluoromethyl, phenyl or phenoxy, and
Y' is hydrogen, fluoro, chloro, bromo, alkyl of 1 to 4 carbon atoms or alkoxy of 1 to 4 carbon atoms, with the proviso that R° is alkyl when R is phenyl or phenyl substituted by fluoro, chloro or bromo.

Other novel compounds provided by the invention are of the formula:

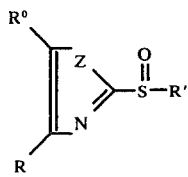

wherein
R' is alkyl of 1 to 6 carbon atoms,
Z is oxygen or sulfur, and
R° and R are independently hydrogen, alkyl of 1 to 6 carbon atoms, phenyl or substituted phenyl of the formula:

in which
Y is fluoro, chloro, bromo, alkyl of 1 to 4 carbon atoms, alkoxy of 1 to 4 carbon atoms, trifluoromethyl, phenyl or phenoxy, and
Y' is hydrogen, fluoro, chloro, bromo, alkyl of 1 to 4 carbon atoms or alkoxy of 1 to 4 carbon atoms, with the proviso that at least one of R° and R is biphenylyl or phenoxyphenyl.

Other novel compounds of the formula I are those in which n is 0 and at least one of R° and R is biphenylyl or phenoxyphenyl. Preferred compounds of such novel class have R° representing hydrogen or alkyl and R representing p-biphenylyl or p-phenoxyphenyl, more preferably, with R being alkyl of 1 to 6 carbon atoms.

What is claimed is:

1. The method of combatting weeds in a locus containing weeds comprising applying to the locus a herbicidally effective amount of a compound of the formula:

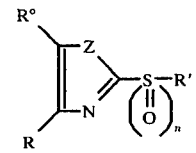

wherein
R° and R are independently hydrogen, alkyl of 1 to 6 carbon atoms, phenyl or substituted phenyl of the formula:

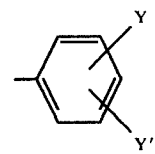

in which
Y is fluoro, chloro, bromo, alkyl of 1 to 4 carbon atoms, alkoxy of 1 to 4 carbon atoms, trifluoromethyl, phenyl or phenoxy, and
Y' is hydrogen, fluoro, chloro, bromo, alkyl of 1 to 4 carbon atoms or alkoxy of 1 to 4 carbon atoms,
R' is alkyl of 1 to 6 carbon atoms,
Z is oxygen or sulfur, and
n is 0, 1 or 2.

2. The method of claim 1 in which n is 1, R° is hydrogen or alkyl of 1 to 6 carbon atoms, R is phenyl or substituted phenyl and Z is oxygen.

3. The method of claim 2 in which R is phenyl or phenyl substituted independently by fluoro, chloro, bromo, alkyl of 1 to 4 carbon atoms, alkoxy of 1 to 4 carbon atoms or trifluoromethyl and R° is alkyl of 1 to 6 carbon atoms.

4. The method of claim 3 in which R is phenyl.

5. The method of claim 4 in which the compound is 5-methyl-2-methylsulfinyl-4-phenyl-oxazole.

6. The method of claim 1 in which Z is sulfur.

7. The method of claim 1 in which Z is oxygen.

8. The method of claim 7 in which n is 1.

9. The method of claim 1 in which n is 1, R° is hydrogen or alkyl or 1 to 6 carbon atoms, R is phenyl or substituted phenyl and Z is sulfur.

10. The method of claim 9 in which R is phenyl or phenyl substituted independently by fluoro, chloro, bromo, alkyl of 1 to 4 carbon atoms, alkoxy of 1 to 4 carbon atoms or trifluoromethyl and R° and is alkyl of 1 to 6 carbon atoms.

11. The method of claim 10 is which R is phenyl.

12. The method of claim 11 in which the compound is 5-methyl-2-methylsulfinyl-4-phenyl-thiazole.

13. The method of claim 1 in which weeds are combatted in a cultivated crop locus selected from the group consisting of wheat, cotton and soya.

14. The method of claim 13 in which n is 1, R° is hydrogen or alkyl of 1 to 6 carbon atoms, R is phenyl or substituted phenyl and Z is sulfur.

15. The method of claim 14 in which R is phenyl or phenyl substituted independently by fluoro, chloro, bromo alkyl of 1 to 4 carbon atoms, alkoxy of 1 to 4 carbon atoms or trifluoromethyl and R° is alkyl of 1 to 6 carbon atoms.

16. The method of claim 15 is which R is phenyl.

17. The method of claim 16 in which the compound 5-methyl-2-methylsulfinyl-4-phenyl-thiazole.

18. A herbicidal composition comprising, as active agent, a herbicidally effective amount of a compound of the formula:

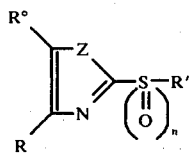

wherein
R° and R are independently hydrogen, alkyl of 1 to 6 carbon atoms, phenyl or substituted phenyl of the formula:

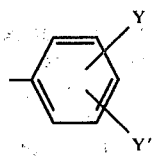

in which
Y is fluoro, chloro, bromo, alkyl of 1 to 4 carbon atoms, alkoxy of 1 to 4 carbon atoms, trifluoromethyl, phenyl or phenoxy, and
Y' is hydrogen, fluoro, chloro, bromo, alkyl of 1 to 4 carbon atoms or alkoxy of 1 to 4 carbon atoms,
R' is alkyl of 1 to 6 carbon atoms,
Z is oxygen or sulfur, and
n is 0, 1 or 2,
in association with a herbicide carrier.

19. The composition of claim 18 in which n is 1, R° is hydrogen or alkyl of 1 to 6 carbon atoms, R is phenyl or substituted phenyl and Z is sulfur.

20. The composition of claim 19 in which R is phenyl or phenyl substituted independently by fluoro, chloro, bromo, alkyl of 1 to 4 carbon atoms, alkoxy of 1 to 4 carbon atoms or trifluoromethyl and R° is alkyl of 1 to 6 carbon atoms.

21. The composition of claim 20 in which R is phenyl.

22. The composition of claim 21 in which the compound is 5-methyl-2-methylsulfinyl-4-phenyl-thiazole.

* * * * *